US012780758B2

(12) United States Patent
Hwang et al.

(10) Patent No.: US 12,780,758 B2
(45) Date of Patent: Nov. 3, 2026

(54) METHOD FOR PREPARING ALPHA-OLEFIN WITH HIGH SELECTIVITY, AND DUAL-BED CATALYST SYSTEM THEREFOR

(71) Applicant: KOREA RESEARCH INSTITUTE OF CHEMICAL TECHNOLOGY, Daejeon (KR)

(72) Inventors: Dong Won Hwang, Daejeon (KR); Gwang Nam Yun, Daejeon (KR); In Yong Eom, Daejeon (KR); Marcel Jonathan Hidajat, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 220 days.

(21) Appl. No.: 18/577,771

(22) PCT Filed: Jun. 29, 2022

(86) PCT No.: PCT/KR2022/009309
§ 371 (c)(1),
(2) Date: Jan. 9, 2024

(87) PCT Pub. No.: WO2023/008753
PCT Pub. Date: Feb. 2, 2023

(65) Prior Publication Data
US 2024/0317655 A1 Sep. 26, 2024

(30) Foreign Application Priority Data
Jul. 29, 2021 (KR) ........................ 10-2021-0099827

(51) Int. Cl.
*C07C 1/24* (2006.01)
*C07C 29/149* (2006.01)

(52) U.S. Cl.
CPC .............. *C07C 1/24* (2013.01); *C07C 29/149* (2013.01); *C07C 2521/04* (2013.01); *C07C 2521/06* (2013.01); *C07C 2521/08* (2013.01)

(58) Field of Classification Search
CPC ..... C07C 1/24; C07C 29/149; C07C 2521/04; C07C 2521/06; C07C 2521/08
See application file for complete search history.

(56) References Cited

U.S. PATENT DOCUMENTS

2013/0030224 A1* 1/2013 Kim ..................... B01J 23/8474
568/885

FOREIGN PATENT DOCUMENTS

JP 06116182 A * 4/1994
JP 6781046 B2 11/2020
(Continued)

OTHER PUBLICATIONS

Onyestyak, G., Harnos, S., Kallo, D., "Improving the catalytic behavior of Ni/Al2O3 by indium in reduction of carboxylic acid to alcohols", Catalysis Communications, 2011, 16, 184-188 (Year: 2011).*
(Continued)

*Primary Examiner* — James C Goloboy
(74) *Attorney, Agent, or Firm* — Harness, Dickey & Pierce, P.L.C.

(57) ABSTRACT

The present invention successively performs hydrodeoxygenation (HDO) and dehydration so that, unlike that of a conventional technique, an alpha-olefin is prepared to have high selectivity, and not an olefin having a double bond at sites other than the alpha position. In addition, according to the present invention, selectivity for alpha-olefin can be further improved under optimal reaction conditions, and an alpha-olefin can be stably prepared with an extended preparation time of up to 180 hours.

11 Claims, 5 Drawing Sheets

(56) References Cited

FOREIGN PATENT DOCUMENTS

| | | | | |
|---|---|---|---|---|
| KR | 10-2013-0025412 A | 3/2013 | | |
| KR | 10-2020-0035953 A | 4/2020 | | |
| WO | WO-2004078336 A2 * | 9/2004 | .............. | B01J 21/04 |

OTHER PUBLICATIONS

Lee, J.-M., Upare, P.P., Chang, J.-S., Hwang, Y.K. Lee, J.H., Hwang, D.W., Hong, D.-Y., Lee, S.H., Jeong, M.-G., Kim, Y.D., Kwon, Y.-U., "Direct Hydrogenation of Biomass-Derived Butyric Acid to n-Butanol over a Ruthenium-Tim Bimetallic Catalysts", ChemSusChem, 2014, 7, 2998-3001 (Year: 2014).*

English-language machine translation of JP 6-116182 A (Year: 1994).*

Witsuthammakul et al., "Selective hydrodeoxygenation of bio-oil derived products: acetic acid to propylene over hybrid CeO2—Cu/zeolite catalysts", Catalysis Science & Technology. 2015, vol. 6, pp. 1737-1745.

Ali et al., "Selective synthesis of a-olefins by dehydration of fatty alcohols over alumina-thoria mixed catalysts", Catalysis science & technology, 2020, pp. 3701-3708.

Vorotnikov et al., "Inverse bimetallic RuSn catalyst for selective carboxylic acid reduction", ACS Catalysis, 2019, pp. 11350-11359.

Yeap et al., "Selectivity control during the single-step conversion of aliphatic carboxylic acids to linear olefins", *ACS Catal.*, 2018, 10769-10773.

International Search Report for International Application No. PCT/KR2022/009309 dated Nov. 3, 2022.

* cited by examiner (a)

(b)

METHOD FOR PREPARING ALPHA-OLEFIN WITH HIGH SELECTIVITY, AND DUAL-BED CATALYST SYSTEM THEREFOR

CROSS-REFERENCE TO RELATED APPLICATIONS

This application is a national phase under 35 U.S.C. § 371 of PCT International Application No. PCT/KR2022/009309 which has an International filing date of Jun. 29, 2022, which claims priority to Korean Application No. 10-2021-0099827, filed Jul. 29, 2021, the entire contents of each of which are hereby incorporated by reference.

TECHNICAL FIELD

The present disclosure relates to a method of preparing an alpha-olefin with high selectivity and a dual-bed catalyst system for the same and, more particularly, to a method of preparing an alpha-olefin with high selectivity from a carboxylic acid compound by performing hydrodeoxygenation and dehydration reactions in series under a hydrogen atmosphere and to a dual-bed catalyst system for the same.

BACKGROUND ART

Petroleum resources used industrially to produce chemicals have limited reserves and problems causing environmental problems such as global warming and climate change, so efforts have been made to replace them with environmentally friendly resources.

Recently, attempts have been made to use a carboxylic acid compound as raw materials to prepare chemicals. The carboxylic acid compound is an oxygen-containing carbon compound in the carboxyl group (—COOH) and are abundant in nature, so they can be easily obtained from biomass resources, thereby increasing interest in the carboxylic acid compound as a sustainable resource. The method of producing alcohol-type biofuel through a reduction reaction by using the carboxylic acid compound has reached the commercialization stage, but to date, the method has been unavailable yet of commercially preparing an alpha-olefin which is a chemical raw material with a high-added value among chemicals obtained from the carboxylic acid compound.

An olefin is generally a compound that refers to alkenes with a double bond between carbons, and generally various olefin-based petrochemical substances are usually produced from Naphtha or heavy oil fractions extracted from crude oil during the refining process. Since these olefins are used as raw materials to prepare synthetic resins and synthetic rubber, olefins can be used in most industrial fields such as automobiles, electronics, construction, and pharmaceuticals.

An alpha-olefin among the olefins is an alkene compound with a double bond at the alpha position and may be used to produce synthetic lubricants, plastics, detergents, and cosmetics. In particular, plastics manufactured by adding alpha-olefins are a fine chemical raw material with a high-added value due to their higher strength than typical plastics so the plastics containing alpha-olefin are highly useful in various industries. Therefore, research and development on methods to commercially prepare an alpha-olefin is actively underway.

As a conventional art in the alpha olefin-related technical field, Non-Patent Document 1 relates to a method of preparing propylene from acetic acid derived from the thermal decomposition of biomass. The document discloses a technology to convert the acetic acid to the propylene through a keto-hydrodeoxygenation (KHDO) reaction in the presence of a $CeO_2$—Cu/zeolite hybrid catalyst. However, the method of preparing propylene in Non-Patent Document 1 discloses that 2 molecules of acetic acid with 2 carbon atoms produce 1 propylene with 3 carbon atoms through a KHDO reaction, and the acetic acid consumes 2 molecules as an initial reactant to produce 1 propylene and 1 $CO_2$, and the method has a problem of low production efficiency. In addition, when an olefin with 4 or more carbon atoms is produced by using a catalyst and through the KHDO reaction, an olefin with a double bond located in a position other than the alpha position is produced due to the locational stability of the double bond on the olefin.

In addition, Non-Patent Document 2 relates to a single-step conversion from aliphatic carboxylic acid to linear olefin, and the document discloses how hexene is produced from $C_6$ hexanoic acid in a single reaction system by using a bifunctional catalyst that simultaneously facilitates hydrogenation (HDO) and dehydration reactions. However, the hexene produced from the hexene preparation method of Non-Patent Document 2 is 2-hexene and 3-hexene which are isomerized compounds of 1-hexene and account for 95% of the total olefin molecules produced. In this regard, the selectivity for an alpha-olefin is low.

DISCLOSURE

Technical Problem

One objective of the present disclosure is to prepare an alpha-olefin with high selectivity by using a dual-bed catalyst system that facilitates hydrodeoxygenation (HDO) and dehydration reactions in series and to provide optimal reaction conditions for the preparation of the alpha-olefin.

Another objective of the present disclosure is to provide a method of stably preparing an alpha-olefin with an extended preparation time of up to 180 hours.

Technical Solution

To solve the problem, the present disclosure may provide a method of preparing an alpha-olefin with high selectivity, the method including:

(a) causing a hydrodeoxygenation reaction to produce alcohol by introducing hydrogen gas and a carboxylic acid compound into a reaction system filled with a hydrodeoxygenation reaction catalyst and removing oxygen from the carboxylic acid compound; and (b) causing a dehydration reaction of the alcohol to produce an alpha-olefin by supplying an effluent from the hydrodeoxygenation reaction to a reaction system filled with a dehydration reaction catalyst, in which the effluent of Step (a) is directly introduced into Step (b).

The carboxylic acid compound may be a carboxylic acid compound having 4 or more carbon atoms, and preferably a carboxylic acid compound having 6 or more carbon atoms.

The hydrodeoxygenation reaction catalyst may be a catalyst in which both Ru and Sn are supported as active metals on a metal oxide, and preferably the molar ratio of Ru and Sn supported on the metal oxide may be 1:2.

The reaction system filled with the hydrodeoxygenation catalyst may have an internal temperature in the range of 250° C. to 400° C.

The dehydration reaction catalyst may be one or more selected from the group consisting of alumina ($Al_2O_3$), zeolite, and silica ($SiO_2$).

The reaction system filled with the dehydration reaction catalyst may have a WHSV in the range of greater than 0.5 $h^{-1}$ and less than 1.75 $h^{-1}$.

In addition, the present disclosure may provide a dual-bed catalyst system with the connection of a hydrodeoxygenation reaction unit and a dehydration reaction unit. The hydrodeoxygenation reaction unit is configured to introduce hydrogen gas and a carboxylic acid compound into a reaction system filled with a hydrodeoxygenation reaction catalyst in a first bed and remove oxygen from the carboxylic acid compound to produce alcohol. The dehydration reaction unit is configured to supply the effluent from the hydrodeoxygenation reaction unit into a reaction system filled with a dehydration reaction catalyst in a second bed and to form an alpha-olefin through a dehydration reaction of the alcohol contained in the effluent.

The hydrodeoxygenation reaction unit and the dehydration reaction unit may be provided in a single reactor or respective reactors and may be interconnected such that the effluent from the hydrodeoxygenation reaction unit is supplied to the dehydration reaction unit.

The hydrodeoxygenation reaction catalyst is a catalyst in which Ru and Sn are both supported on a carrier, and the dehydration reaction catalyst may be one or more selected from the group consisting of alumina, zeolite, and silica.

Advantageous Effects

The present disclosure can achieve a remarkable effect in preparing an alpha-olefin with high selectivity by performing hydrodeoxygenation (HDO) and dehydration reactions in series rather than preparing an olefin with a double bond located in a position other than the alpha position as in the conventional art.

In addition, according to the present disclosure, selectivity for an alpha-olefin can be further improved under optimal reaction conditions, and an alpha-olefin can be stably prepared with an extended preparation time of for up to 180 hours.

MODE FOR DISCLOSURE

Figure 1:
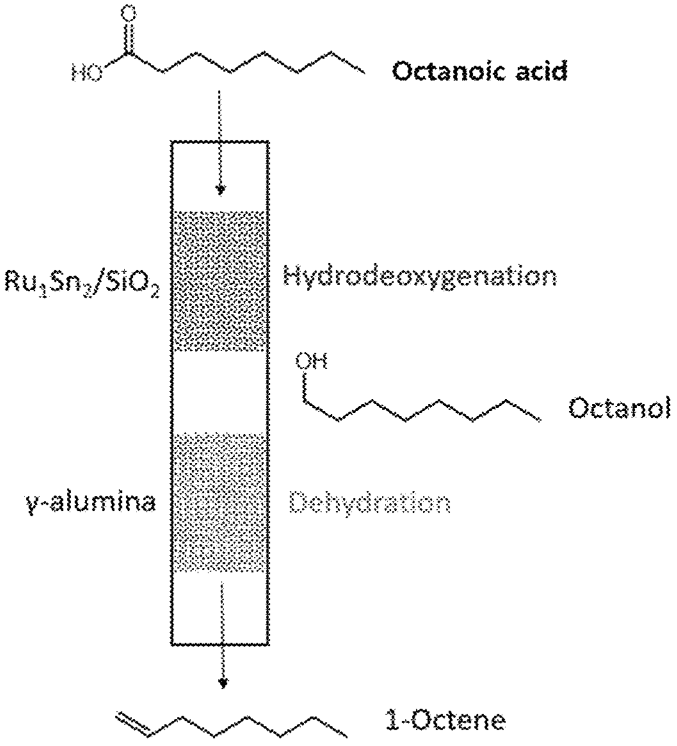
FIG. 1 is a schematic diagram illustrating a reaction for producing 1-octene from octanoic acid, according to one embodiment of the present disclosure.

Throughout the specification of the present application, when a part "includes" a certain component, this means that it may further include other components rather than excluding other components unless specifically stated to the contrary.

The present disclosure relates to a method of preparing an alpha-olefin with high selectivity and a dual-bed catalyst system for the same. Since hydrodeoxygenation and dehydration reactions are linearly connected in series to enable a chain reaction, the reactions continue to be performed under the supply of hydrogen gas, and the present disclosure has its feature of preparing an alpha-olefin with high selectivity.

A characteristic configuration of the present disclosure is that a carboxylic acid compound is converted into an alcohol compound that is an intermediate product obtained through the hydrodeoxygenation and dehydration reactions performed in a series as the reactions are linearly connected in a reaction system. The conversion configuration is different from that of the keto-hydrodeoxygenation (KHDO) reaction in which carbon dioxide and water molecules are removed from 2 molecules of acetic acid to form 1 propanone as an intermediate product as in conventional Non-Patent Document 1. In addition, an olefin produced through the KHDO reaction on the carboxylic acid compound with 4 or more carbon atoms may be a beta- or gamma-olefin rather than an alpha-olefin due to thermodynamic stability as the carboxylic acid compound is capable of forming its isomers.

In addition, as in Non-Patent Document 2, the reaction of producing hexene from $C_6$ hexanoic acid in the presence of a bifunctional catalyst that simultaneously facilitates hydrogenation and dehydration reactions in a single reaction system eventually results in an olefin. 95% of the olefin accounts for 2-hexene and 3-hexene with a double bond located in the beta and gamma positions, so the conventional Non-Patent Documents are not suitable for application to a technology of preparing an alpha-olefin with high-selectivity.

Accordingly, the applicant (s) came up with the present disclosure, which may selectively prepare an alpha-olefin with high selectivity through hydrodeoxygenation (HDO) and dehydration reactions in series. In terms of the preparation efficiency of the final product olefin based on the molar number of the introduced carboxylic acid compound, the present disclosure consumes 1 molecule of the reactants while Non-Patent Documents 1 and 2 consume 2 molecules of the reactants, respectively. Given that, the present disclosure is more suitable as a technology to commercially prepare an alpha-olefin.

Hereinafter, a method of preparing an alpha-olefin with high selectivity and a dual-bed catalyst system for the same will be described in detail according to examples of the present disclosure.

The method of preparing the alpha-olefin with high selectivity includes:

(a) causing a hydrodeoxygenation reaction to produce alcohol by introducing hydrogen gas and a carboxylic acid compound into a reaction system filled with a hydrodeoxygenation reaction catalyst and removing oxygen from the carboxylic acid compound; and (b) causing a dehydration reaction of the alcohol to produce an alpha-olefin by supplying an effluent from the hydrodeoxygenation reaction to a reaction system filled with a dehydration reaction catalyst, in which the effluent from Step (a) is directly introduced into Step (b).

FIG. 1 is a schematic diagram illustrating a reaction to prepare 1-octene from octanoic acid as an example of the present disclosure.

Referring to FIG. 1, the dual-bed catalyst system to prepare the alpha-olefin with high selectivity has each reaction system filled with a reaction catalyst for hydrodeoxygenation (HDO) and dehydration reactions and linearly connected in series. As an example of the carboxylic acid compound, when octanoic acid is supplied, it is converted through the hydrodeoxygenation (HDO) reaction to form 1-octanol (an intermediate product), and sequentially 1-octene (an alpha-olefin) is formed through the dehydration reaction.

In addition, the reaction product according to the present disclosure is ideally an alpha-olefin converted from a carboxylic acid compound, but an alpha-olefin with a reduced carbon number may be produced due to a decarbonization reaction which induces the removal of CO or $CO_2$, and also saturated hydrocarbons (paraffin) may be produced by saturating the alpha-olefin with the hydrogen contained in the reaction system.

The carboxylic acid compound that may be applied as a reactant may be unlimitedly used as long as it is a compound containing a carboxyl group (—COOH), but preferably, a carboxylic acid compound having 4 or more carbon atoms, preferably 6 or more carbon atoms, may be used. To enable a gas phase reaction, the alpha-olefin with high selectivity may be prepared by using a carboxylic acid compound having 16 or fewer carbon atoms, preferably 12 or less.

The hydrodeoxygenation reaction catalyst may be an active metal supported by both Ru and Sn.

In addition, the catalyst is supported by both Ru and Sn which may have a molar ratio in the range of 1:0.1 to 1:5, preferably in a range of 1:1 to 1:2, and most preferably, 1:2.

The Ru—Sn carrier is not particularly limited, but any one selected from the group consisting of $SiO_2$, $Al_2O_3$, $CeO_2$, $TiO_2$, and ZnO may be used as the carrier, and preferably, $SiO_2$ may be used.

The hydrodeoxygenation reaction catalyst can be prepared through already-known non-limiting methods such as a wet method, an immersion method, and a coprecipitation method, and preferably, through a coprecipitation method.

The reaction system filled with the hydrodeoxygenation catalyst may have a temperature in the range of 250° C. to 400° C., preferably 300° C. to 375° C., more preferably 325° C. to 375° C. When the temperature is less than 250° C., the conversion rate of carboxylic acid is lowered, and the selectivity of aldehyde (an intermediate product) increases. When the temperature is higher than 400° C., the production of CO and $CO_2$ increases due to the decarbonization reaction.

The hydrogen gas in the reaction system filled with the hydrodeoxygenation reaction catalyst may have a pressure in the range of 10 to 30 bar, and preferably, the pressure may be in the range of 20 to 30 bar. When the pressure is less than 10 bar, the conversion rate of a carboxylic acid is lowered, and the selectivity of aldehyde (an intermediate product) increases.

The dehydration reaction catalyst in step (b) may be one or more selected from the group consisting of alumina, zeolite, and silica, preferably alumina, and more preferably γ-alumina.

The reaction system filled with the dehydration reaction catalyst may have a temperature in the range of 300° C. to 400° C., preferably 300° C. to 375° C., more preferably 325° C. to 375° C. When the temperature is less than 300° C., the conversion rate of alcohol to 1-octene is lowered, and the selectivity for by-products such as ethers increases, and when the temperature exceeds 400° C., more beta- or gamma-olefin is produced due to thermodynamic stability.

The reaction system filled with the dehydration reaction catalyst may have a WHSV of greater than 0.5 $h^{-1}$ and less than 1.75 $h^{-1}$, and preferably the WHSV may be in the range of 0.75 $h^{-1}$ to 1.5 $h^{-1}$. When the WHSV is equal to or less than 0.5 $h^{-1}$, the selectivity for an alpha-olefin decreases, and the selectivity for a beta- or gamma-olefin increases, and when the WHSV is more than 1.75 $h^{-1}$, the conversion of alcohol decreases, and the selectivity for octane increases, so the yield of alpha-olefins is lowered.

The dehydration reaction catalyst may be prepared through already-known non-limiting methods such as the Bayer process, and preferably through a hydrolysis.

Meanwhile, the present disclosure may provide a dual-bed catalyst system to prepare the alpha-olefin with high selectivity.

The dual-bed catalyst system has the connection of a hydrodeoxygenation reaction unit and a dehydration reaction unit of the present disclosure. Herein, the hydrodeoxygenation reaction unit is configured to introduce hydrogen gas and a carboxylic acid compound into the reaction system filled with the hydrodeoxygenation reaction catalyst in a first bed and to remove oxygen from the carboxylic acid compound to produce alcohol. The dehydration reaction unit is configured to supply an effluent from the hydrodeoxygenation reaction unit into the reaction system filled with the dehydration reaction catalyst in a second bed and form the alpha-olefin through the dehydration reaction of the alcohol contained in the effluent.

As shown in FIG. 1, the hydrodeoxygenation reaction unit and dehydration reaction unit may be provided in a single reactor as an example or in respective reactors as another example. As long as the two units are in connection, and the effluent from the hydrodeoxygenation reaction unit is directly supplied to the dehydration reaction unit without any special treatment, there are no restrictions on the location of the hydrodeoxygenation reaction unit and dehydration reaction unit within the reactor, the type and number of reactors is not limited.

In addition, the dual-bed catalyst system is used to perform a chain reaction by linearly connecting the hydrodeoxygenation and dehydration reactions in series and then have the effluent from the hydrodeoxygenation reaction subjected to the dehydration reaction to prepare the alpha-olefin with high selectivity. The matters described in the preparation method may be equally applied to the dual-bed catalyst system, so redundant techniques will be omitted to prevent confusion in understanding the true meaning of the disclosure.

Hereinafter, the present disclosure will be described in more detail through preferred examples.

Preparation Example 1: Preparation of Ru/SiO2 Hydrodeoxygenation Catalyst

Figure 2:
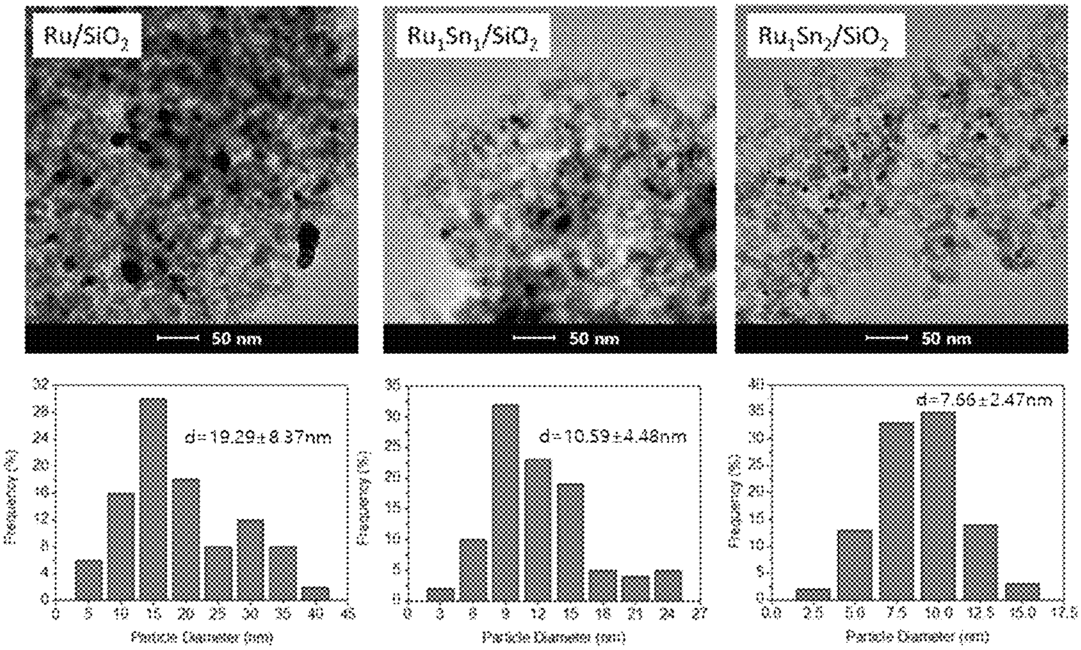
FIG. 2 illustrates TEM images of a cross-section and particle size distribution of a catalyst used in the preferred embodiment of the present disclosure.

A solution of a supported catalyst precursor was prepared by adding and dissolving 0.287 g of $RuCl_3 \times (H_2O)$ in 15 ml of distilled water. Afterward, the prepared solution was placed in a burette. 10 g of silica was added to a 1000 ml beaker, and the solution contained in a burette to the beaker was added drop by drop while continuing to mix the solution. As a result, a silica support with the catalyst precursor supported was prepared. The support was dried at 110° C. for 24 hours and powdered. Afterwards, it was fired at 460° C. for 4 hours under atmospheric pressure. After firing, the result was shaped into a pellet form, and 1 g of the pellet was placed in a quartz reactor. The pellet was subjected to a hydrogen flow at a speed of 100 ml/min and a temperature rise to 460° C. by setting the temperature increase rate to 5° C./min. The pellet was maintained at a temperature of 460° C. for 4 hours, and then the temperature was lowered to room temperature. Afterward, the pellet was treated with 0.2 vol % $O_2$ gas at a flow rate of 100 ml/min at room temperature (about 25° C.) for 4 hours and stored in a glove box to obtain a $Ru/SiO_2$ hydrodeoxygenation catalyst. The photos of the TEM cross-section and particle diameter of the catalyst are shown in FIG. 2.

Preparation Example 2: Preparation of Ru1Sn1/SiO2 Hydrodeoxygenation Catalyst The same method as Preparation Example 1 was performed except that 0.287 g of $RuCl_3 \times (H_2O)$ and 0.485 g of $SnCl_45H_2O$ were added and dissolved in 15 ml of distilled water to prepare a solution of a supported catalyst precursor, thereby $Ru_1Sn_1/SiO_2$ Hydrodeoxygenation catalyst was obtained. The photos of the TEM cross-section and particle diameter of the catalyst are shown in FIG. 2.

Preparation Example 3: Preparation of Ru1Sn2/$SiO_2$ Hydrodeoxygenation Catalyst The same method as Preparation Example 1 was performed except that 0.287 g of $RuCl_3 \times (H_2O)$ and 0.971 g of $SnCl_45H_2O$ were added and dissolved in 15 ml of distilled water to prepare a solution of a supported catalyst precursor, $Ru_1Sn_2/SiO_2$ Hydrodeoxygenation catalyst was obtained. The photos of the TEM cross-section and particle diameter of the catalyst are shown in FIG. 2.

Preparation Example 4: Dehydration Reaction Catalyst

γ-alumina prepared by Alfa Aesar was purchased and used as a dehydration reaction catalyst.

Figure 3:
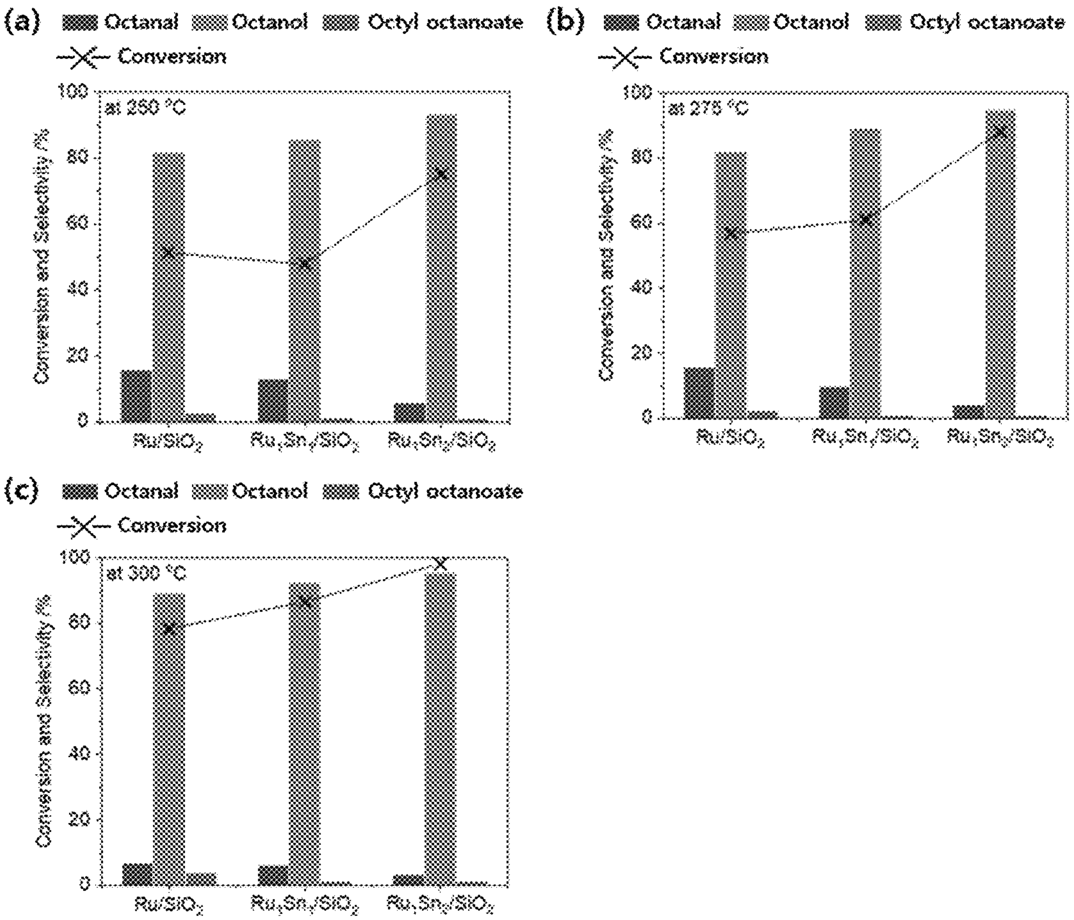
FIGS. 3(*a*), 3(*b*), and 3(*c*) are graphs illustrating the conversion rate and selectivity of the catalyst used in the preferred embodiment of the present disclosure at (a) 250° C., (b) 275° C., and (c) 300° C., respectively.

Experimental Example 1: Conversion Rate and Selectivity According to Active Metal Composition in Catalyst and Hydrodeoxygenation Reaction Temperature After 0.5 g of the hydrodeoxygenation reaction catalyst of Preparation Examples 1 to 3 was charged into the first bed in the hydrodeoxygenation reaction system of the reactor, a reaction gas containing octanoic acid ($C_8H_{15}COOH$) was supplied at a flow rate of 0.02 ml/min, and hydrogen gas was supplied at a flow rate of 200 ml/min so that the pressure was 20 atm, and the molar ratio of hydrogen gas and reaction gas was 70.75. The hydrodeoxygenation reaction was performed under the conditions: a temperature in the range of 250° C. to 300° C. in the reaction system and a WHSV of 2 $h^{-1}$. The results are shown in FIGS. 3(*a*) to 3(*c*).

As for the hydrodeoxygenation reaction results, the conversion rate and selectivity of 1-octanol (an intermediate product of the reaction for the alpha-olefin), 1-octanal (a by-product), and octyl octanoate (a by-product) were calculated using the formula below.

[Calculation Formula for Conversion Rate]

$$\text{Conversion (\%)} = \left(1 - \frac{\text{mol of octanoic acid in product}}{\text{mol of injected octanoic acid}}\right) \times 100$$

[Calculation Formula for Selectivity]

$$S_i = \text{Selectivity of product } i \text{ (\%)} = \left(\frac{v_i n_i}{\sum v_i n_i}\right) \times 100$$

$v_i$=number of carbon atoms in compound i $n_i$=number of moles of compound i

Looking at the effect of reaction temperature on the hydrodeoxygenation reaction to produce the intermediate product for the alpha-olefin with reference to FIGS. 3(*a*) to 3(*c*), the conversion rate tends to increase as the reaction temperature increases from 250° C. to 300° C. In particular, in the case of the reaction temperature of 275° C. or higher, the conversion rate of the catalyst supported with Ru and Sn at a molar ratio of 1:2 was found to be excellent, exceeding 85%.

In addition, looking at the effect of the active metal composition in the catalyst on the hydrodeoxygenation reaction, the conversion rate of the catalyst and selectivity for octanol that is an intermediate product of octanoic acid was found to be excellent when the catalyst was supported by both Ru and Sn as active metals rather than supported by Ru alone. In particular, when the HDO reaction temperature was 275° C., the catalyst supported by both Ru and Sn at a molar ratio of 1:2 showed a 30% increase in the conversion rate compared to the catalyst supported by Ru alone, and the octanol selectivity increased by up to 10%.

Experimental Example 2: Measurement of Conversion Rate and Selectivity According to Temperature in Dual-Bed Reactor To identify the effect of temperature in the dual-bed reactor, 1.0 g of $Ru_1Sn_2/SiO_2$ as a hydrodeoxygenation reaction catalyst was charged into the upper part of a stainless steel reactor with a diameter of 0.5 inches, and 0.5 g of γ-alumina as the dehydration reaction catalyst was charged into the lower part of the reactor. The temperature of the reactor was raised to a set range while hydrogen flowed into the reactor. Afterward, octanoic acid ($C_8H_{15}COOH$) and hydrogen were supplied to the upper part of the reactor at a flow rate of 0.018 ml/min and 180 ml/min, respectively. At this time, the gases were supplied to raise the reaction pressure to 20 atm, and the molar ratio of hydrogen gas and reaction gas was 70.75. To identify the effect of reaction temperature, hydrodeoxygenation-dehydration reactions were performed while changing the temperature in the reactor in the range of 300° C. to 400° C. The results are shown in FIG. 4(*a*).

Figure 4:
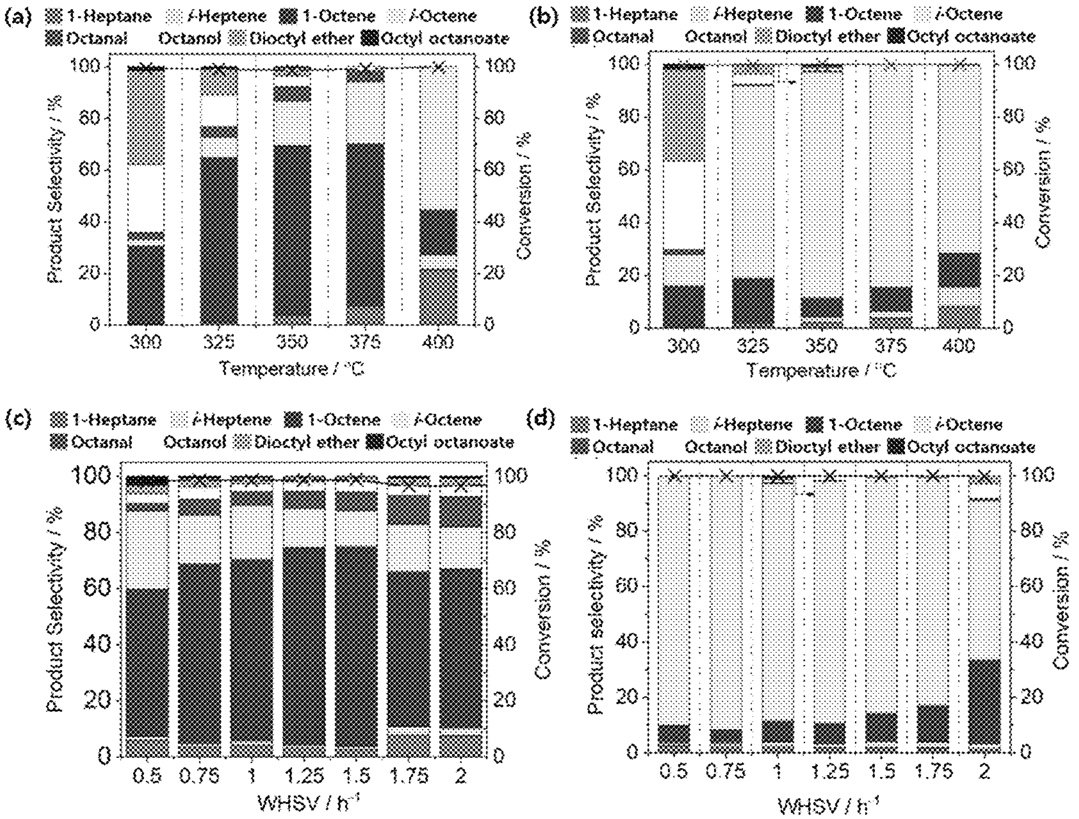
FIGS. 4(*a*), 4(*b*), 4(*c*), and 4(*d*) are graphs illustrating the conversion rate and selectivity according to changes in (a) reaction temperature of the dual-bed catalyst system and (b) WHSV of the dual-bed catalyst system, (c) reaction temperature of the single-bed catalyst system and (d) WHSV of the single-bed catalyst system in the preparation method of the present disclosure.

In FIG. 4(*a*), the conversion rate was close to 100% in the reaction temperature range of 300° C. to 400° C., and as the reaction temperature increased, reaction intermediate products including 1-octanol and dioctylether gradually decreased. Especially, when the temperature of the reactor was in the range between 325° C. and 375° C., the selectivity for 1-octene which was an alpha-olefin was found to exceed 60%.

On the other hand, when the reaction temperature exceeds 375° C., the selectivity for 1-octene (the target product) decreases rapidly, and iso-octene (an isomer of 1-octene), iso-heptene (a decarbonized compound), and 1-heptene (a saturated hydrocarbon of iso-heptene) increased.

Experimental Example 3: Measurement of Conversion Rate and Selectivity According to Temperature in Single-Bed Reactor To identify the effect of temperature in the Single-bed reactor, 1.0 g of $Ru_1Sn_2/SiO_2$ as a hydrodeoxygenation reaction catalyst and 0.5 g of γ-alumina as a dehydration reaction catalyst were mixed and charged into a stainless steel reactor with a diameter of 0.5 inches. The temperature of the reactor was raised to a set range while hydrogen flowed into the reactor. Afterward, octanoic acid ($C_8H_{15}COOH$) and hydrogen were supplied to the upper part of the reactor at a flow rate of 0.018 ml/min and 180 ml/min, respectively. At this time, the gases were supplied to raise the reaction pressure to 20 atm, and the molar ratio of hydrogen gas and reaction gas was 70.75. To identify the effect of reaction temperature, hydrodeoxygenation-dehydration reactions were performed while changing the temperature in the reactor in the range of 300° C. to 400° C. The results are shown in FIG. 4(*b*).

In FIG. 4(*b*), the conversion rate was close to 100% in the reaction temperature range of 300° C. to 400° C. When the temperature was above 325° C., iso-octene was mainly produced, and the selectivity for 1-octene was less than 20%.

Meanwhile, when the reaction temperature exceeded 400° C., the selectivity for iso-heptene (a decarbonized compound) and 1-heptene (a saturated hydrocarbon of iso-heptene) was found to increase.

Experimental Example 4: Measurement of Conversion Rate and Selectivity According to Space Velocity in Dual-Bed Reactor To identify the effect of space velocity in the Dual-bed reactor, 1.0 g of $Ru_1Sn_2/SiO_2$ as a hydrodeoxygenation reaction catalyst was charged into the upper part of a stainless steel reactor with a diameter of 0.5 inches, and 0.5 g of γ-alumina as a dehydration reaction catalyst was charged into the lower part of the stainless steel reactor. Next, the temperature of the reactor was raised to 350° C. while hydrogen flowed into the reactor. Afterward, octanoic acid ($C_8H_{15}COOH$) and hydrogen gas were supplied to the upper part of the reactor at a flow rate of 0.009 to 0.028 ml/min and 90 to 280 ml/min, respectively. At this time, the gases were supplied to raise the reaction pressure to 20 atm, and the molar ratio of hydrogen gas and reaction gas was 70.75. To identify the effect of WHSV, a hydrodeoxygenation reaction was performed while changing the WHSV in the reactor in the range of 0.5 $h^{-1}$ to 1.5 $h^{-1}$. The results are shown in FIG. 4(*c*).

Looking at the effect of space velocity on the hydrodeoxygenation and dehydration reactions with reference to FIG. 4(*c*), in the section where WHSV increased from 0.50 $h^{-1}$ to 1.50 $h^{-1}$, the conversion rate was close to 100%, and as the reaction intermediate products including 1-octanol and dioctylether gradually decreased, the selectivity for 1-octene increased, reaching a maximum of more than 70% under a WHSV condition of 1.50 $h^{-1}$.

Experimental Example 5: Measurement of Conversion Rate and Selectivity According to Space Velocity in Single-Bed Reactor To identify the effect of space velocity in the Single-bed reactor, 1.0 g of $Ru_1Sn_2/SiO_2$ as a hydrodeoxygenation reaction catalyst and 0.5 g of γ-alumina as a dehydration reaction catalyst were mixed and charged into a stainless steel reactor with a diameter of 0.5 inches, and the temperature of the reactor was raised to 350° C. while hydrogen flowed into the reactor. Afterward, octanoic acid ($C_8H_{15}COOH$) and hydrogen gas were supplied to the upper part of the reactor at a flow rate of 0.009 to 0.028 ml/min and 90 to 280 ml/min, respectively. At this time, the gases were supplied to raise the reaction pressure to 20 atm, and the molar ratio of hydrogen gas and reaction gas was 70.75. To identify the effect of WHSV, a hydrodeoxygenation reaction was performed while changing the WHSV in the reactor in the range of 0.5 $h^{-1}$ to 1.5 $h^{-1}$. The results are shown in FIG. 4(*d*).

Looking at the effect of space velocity on the hydrodeoxygenation and dehydration reactions with reference to FIG. 4(*d*), in the section where WHSV increased from 0.50 $h^{-1}$ to 1.50 $h^{-1}$, the conversion rate was close to 100, and iso-octene (with a selectivity of 85% to 90%) was mainly produced. The selectivity for 1-octene reached a maximum of 10% under a WHSV condition of 1.50 $h^{-1}$.

Experimental Example 6: Long-Term Stability Test

To test the long-term stability of the reaction system according to the present disclosure, in Experimental Example 2, the reactions were performed in series for 180 hours at fixed conditions: a reaction temperature of 350° C., a reaction pressure of 20 bar, a WHSV of 1.5 $h^{-1}$, and a molar ratio of hydrogen/feed of 70.75. The results are shown in FIG. 5.

Figure 5:
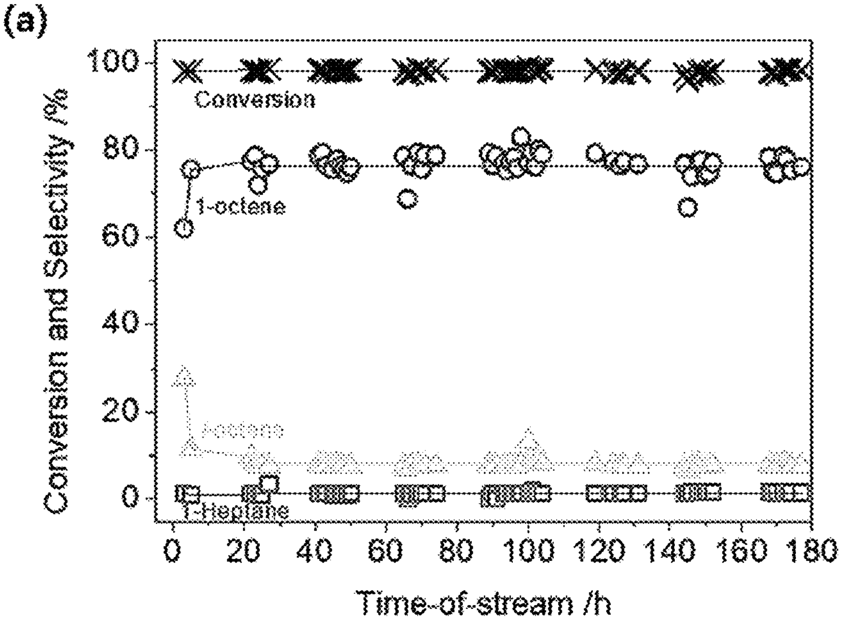
FIG. 5 illustrates photos showing the conversion rate and selectivity over time in the preparation method of the present disclosure.
Figure 5:
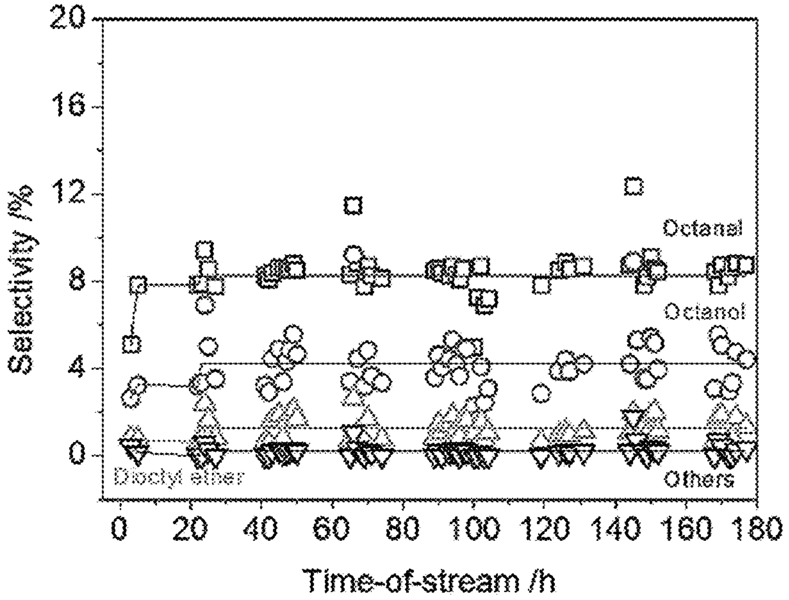

Referring to FIG. 5, in terms of the conversion rate and composition of the hydrodeoxygenation and dehydration reaction products over time, 1-octene was stably produced while the selectivity for 1-octene was maintained at more than 75% in 5 hours of the reaction gas supply, and the selectivity for iso-octene which was an isomer of 1-octene was maintained below 10%.

The present disclosure has been described above with reference to the examples shown in the attached drawings, but these examples are merely illustrative, and various modifications and other equivalent embodiments can be made by those skilled in the art. Therefore, the scope of technical protection of the present disclosure should be determined by the scope of the patent claims below.

The invention claimed is:

1. A method of preparing an alpha-olefin with high selectivity, the method comprising:

(a) causing a hydrodeoxygenation reaction to produce alcohol by introducing hydrogen gas and a carboxylic acid compound into a reaction system filled with a hydrodeoxygenation reaction catalyst and removing oxygen from the carboxylic acid compound; and (b) causing a dehydration reaction of the alcohol to produce the alpha-olefin by supplying an effluent from the hydrodeoxygenation reaction to a reaction system filled with a dehydration reaction catalyst, wherein the effluent of Step (a) is directly introduced into Step (b), and wherein the reaction system filled with the dehydration reaction catalyst has a WHSV of greater than 0.5 $h^{-1}$ and less than 1.75 $h^{-1}$.

2. The method of claim 1, wherein the carboxylic acid compound is a carboxylic acid compound having 4 to 16 carbon atoms.

3. The method of claim 2, wherein the carboxylic acid compound is a carboxylic acid compound having 6 to 12 carbon atoms.

4. The method of claim 1, wherein the hydrodeoxygenation reaction catalyst comprises both Ru and Sn supported as active metals.

5. The method of claim 1, wherein the hydrodeoxygenation reaction catalyst comprises both Ru and Sn supported as active metals, and the dehydration reaction catalyst is one or more selected from the group consisting of alumina, zeolite, and silica.

6. The method of claim 5, wherein Ru and Sn in the hydrodeoxygenation reaction catalyst are supported in a molar ratio of 1:2.

7. The method of claim 1, wherein the reaction system filled with the hydrodeoxygenation reaction catalyst has a temperature in a range of 250° C. to 400° C.

8. A dual-bed catalyst system to prepare an alpha-olefin with high selectivity, the dual-bed catalyst system comprising:

a hydrodeoxygenation reaction unit configured to introduce hydrogen gas and a carboxylic acid compound into a reaction system filled with a hydrodeoxygenation reaction catalyst and to remove oxygen from the carboxylic acid compound, thereby producing alcohol; and a dehydration reaction unit connected in series with the hydrodeoxygenation reaction unit, the dehydration reaction unit configured to receive an effluent from the hydrodeoxygenation reaction unit and to supply the effluent to a reaction system filled with a dehydration reaction catalyst and to form the alpha-olefin through a dehydration reaction of the alcohol contained in the effluent, wherein the hydrodeoxygenation reaction catalyst is supported on a carrier, wherein the carrier is at least one of $SiO_2$, $Al_2O_3$, $CeO_2$, and $TiO_2$, and wherein the dehydration reaction unit is configured to supply the effluent to the reaction system filled with the dehydration reaction catalyst at a rate such that the reaction system filled with the dehydration reaction catalyst is configured to have a WHSV of greater than 0.5 $h^{-1}$ and less than 1.75 $h^{-1}$.

9. The dual-bed catalyst system of claim 8, wherein the hydrodeoxygenation reaction unit and the dehydration reaction unit are provided in a single reactor and are connected such that the effluent from the hydrodeoxygenation reaction unit is supplied to the dehydration reaction unit.

10. The dual-bed catalyst system of claim 8, wherein the hydrodeoxygenation reaction catalyst includes both Ru and Sn supported on the carrier, and the dehydration reaction catalyst is one or more selected from the group consisting of alumina, zeolite, and silica.

11. The dual-bed catalyst system of claim 8, wherein the hydrodeoxygenation reaction unit and the dehydration reaction unit are provided in respective reactors which are connected such that the effluent from the hydrodeoxygenation reaction unit is supplied to the dehydration reaction unit.

* * * * *